United States Patent
Dorsch et al.

(10) Patent No.: US 7,244,846 B2
(45) Date of Patent: Jul. 17, 2007

(54) SUBSTITUTED BENZOFURAN-2-CARBOXAMIDES DERIVATIVES

(75) Inventors: Dieter Dorsch, Ober-Ramstadt (DE); Henning Boettcher, Darmstadt (DE); Christoph van Amsterdam, Darmstadt (DE); Wilfried Rautenberg, Reinheim (DE); Gerd Bartoszyk, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 425 days.

(21) Appl. No.: 10/471,584

(22) PCT Filed: Feb. 27, 2002

(86) PCT No.: PCT/EP02/02093

§ 371 (c)(1), (2), (4) Date: Sep. 12, 2003

(87) PCT Pub. No.: WO02/083666

PCT Pub. Date: Oct. 24, 2002

(65) Prior Publication Data

US 2005/0075269 A1    Apr. 7, 2005

(30) Foreign Application Priority Data

Mar. 14, 2001 (DE) ................ 101 12 151

(51) Int. Cl.
*A61K 31/495* (2006.01)
*C07D 405/10* (2006.01)

(52) U.S. Cl. ............... 544/373; 546/201; 514/254; 514/323

(58) Field of Classification Search ........... 514/254, 514/323; 544/373; 546/201
See application file for complete search history.

(56) References Cited

U.S. PATENT DOCUMENTS 5,532,241 A * 7/1996 Bottcher et al. ...... 514/254.09

6,251,908 B1 * 6/2001 Bottcher et al. ...... 514/254.09

FOREIGN PATENT DOCUMENTS

| HU | P9402806 | 1/1993 |
| HU | P0002718 | 10/2001 |
| WO | WO 99/03855 | 1/1999 |
| WO | WO 00/72832 | 12/2000 |

* cited by examiner

*Primary Examiner*—James O. Wilson
*Assistant Examiner*—Paul V. Ward
(74) *Attorney, Agent, or Firm*—Millen, White, Zelano, Branigan, P.C.

(57) ABSTRACT

Compounds of the formula (I), in which D, $R^1$, $R^2$ and n are defined in Claim 1, are potent $5\text{-HT}_{1A}$ agonists and 5-HT reuptake inhibitors and are suitable for the treatment of depression, anxiety states, panic attacks, obsessive-compulsive disorders, psychiatric illnesses, cerebral infarction, cerebral ischaemia, tension states, side-effects in the treatment of high blood pressure, for the prophylaxis and therapy of cerebral illnesses, acromegaly, hypogonadism, secondary amenorrhoea, premenstrual syndrome, undesired puerperal lactation, pain, sleep disorders, narcolepsy, bipolar illnesses, mania, dementia, addiction illnesses, sexual dysfunction, eating disorders, obesity or fibromyalgia (I)

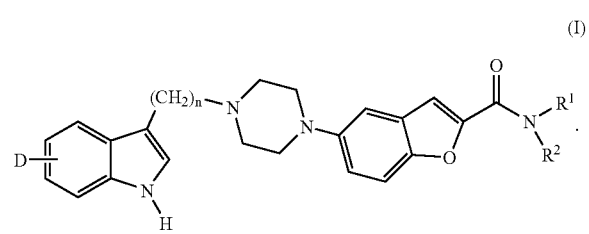

19 Claims, No Drawings

SUBSTITUTED BENZOFURAN-2-CARBOXAMIDES DERIVATIVES

The invention relates to substituted benzofuran-2-carboxamides of the formula I

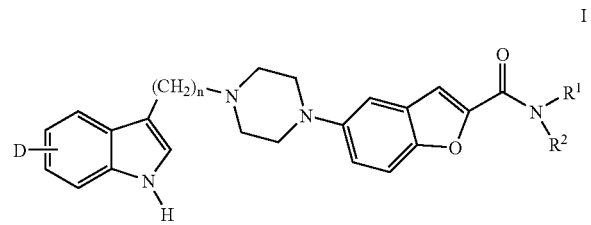

in which
D is H, OH, OA, CN, Hal, COR$^3$ or CH$_2$R$^3$,
R$^1$ is amino, hydroxyl, cyano, —C(=NR$^4$)—N(R$^4$)$_2$, Het, unsubstituted or A-substituted cycloalkyl having from 3 to 10 carbon atoms, or unbranched or branched alkyl having from 1 to 10 carbon atoms, with the proviso that at least one CH$_2$ group in the alkyl group has been replaced by an O or S atom, by a CH=CH group or by a C≡C group, or with the proviso that at least one hydrogen atom in the alkyl group has been replaced by Hal, OH, Ar, Het, cycloalkyl having from 3 to 10 carbon atoms, N(R$^4$)$_2$, CN, COOR$^4$, CON(R$^4$)$_2$, NR$^4$COR$^4$, NR$^4$COOR$^4$, NR$^4$CON(R$^4$)$_2$, NR$^4$SO$_2$ or SO$_2$NR$^4$,
R$^2$ is H, A or R$^1$, with the proviso that, if R$^1$ is amino, hydroxyl or cyano, R$^2$ is H, or
NR$^1$R$^2$ together is a three- to 7-membered saturated heterocyclic ring, in which, in addition, 1 or 2 N and/or 1 or 2 S and/or 1 or 2 O atoms and/or one S(O)$_m$ group, which may be substituted by A, Hal, cycloalkyl having from 3 to 10 carbon atoms, OR$^4$, N(R$^4$)$_2$, CN, COOR$^4$, CON(R$^4$)$_2$, NR$^4$COR$^4$ and/or carbonyl oxygen, may be present,
R$^3$ is OH, OA or N(R$^4$)$_2$,
R$^4$ is H or A,
A is unbranched or branched alkyl having from 1 to 6 carbon atoms, in which at least one CH$_2$ group may be replaced by an O or S atom or by a CH=CH group, or at least one H atom may be replaced by F,
Ar is phenyl, naphthyl or biphenyl, each of which is unsubstituted or monosubstituted or polysubstituted by Hal, A, OR$^4$, N(R$^4$)$_2$, NO$_2$, CN, COOR$^4$, CON(R$^4$)$_2$, NR$^4$COR$^4$, NR$^4$CON(R$^4$)$_2$, NR$^4$SO$_2$A, COR$^4$, SO$_2$NR$^4$ or S(O)$_m$A,
Het is a saturated, unsaturated or aromatic monocyclic or bicyclic heterocyclic radical having from 5 to 10 ring members, in which from 1 to 4 N and/or from 1 to 4 S and/or from 1 to 4 O atoms may be present, and the heterocyclic radical may be monosubstituted, disubstituted or trisubstituted by Hal, A, —[C(R$^4$)$_2$]$_o$—Ar, —[C(R$^4$)$_2$]$_o$-cycloalkyl, OR$^4$, N(R$^4$)$_2$, NO$_2$, CN, COOR$^4$, CON(R$^4$)$_2$, NR$^4$COA, NR$^4$CON(R$^4$)$_2$, NR$^4$SO$_2$A, COR$^4$, SO$_2$NR$^4$ or S(O)$_m$A and/or carbonyl oxygen,
Hal is F, Cl, Br or I,
n is 2, 3, 4 or 5,
m is 1 or 2,
o is 0, 1, 2, 3 or 4, and their physiologically acceptable salts and solvates.

Similar compounds are disclosed in U.S. Pat. No. 5,532,241.

The invention had the object of finding novel compounds having valuable properties, in particular those which can be used for the preparation of medicaments.

It has been found that the compounds of the formula I and their physiologically acceptable salts and solvates are well tolerated and have valuable pharmacological properties since they have actions on the central nervous system. Surprisingly, the compounds simultaneously have selective affinity to 5-HT$_{1A}$ receptors and a selective 5-HT reuptake inhibiting action. In particular, they are combined 5-HT$_{1A}$ agonists and selective 5-HT reuptake inhibitors (SSRIs).

Compounds of the formula I inhibit the binding of tritiated serotonin ligands to hippocampal receptors (Cossery et al., European J. Pharmacol. 1987, 140, 143–155). In addition, changes in DOPA accumulation in the striatum and in 5-HTP accumulation in N. raphe occur (Seyfried et al., European J. Pharmacol. 1989, 160, 31–41). The compounds of the formula I and their physiologically acceptable salts and solvates are therefore suitable medicament active ingredients for antihypertonic agents. They are likewise suitable for the prophylaxis and combating of the consequences of cerebral infarction (apoplexia cerebri), such as strokes and cerebral ischaemia.

In-vitro detection of 5-HT reuptake inhibition is obtained using synaptosomal uptake inhibition (Wong et al., Neuropsychopharmacology 1993, 8, 22–33). This property is investigated ex vivo in mouse brain tissue by the Waldmeier method (European J. Pharmacol. 1977, 46, 387–92). The 5-HT$_{1A}$ agonistic action is detected in vitro by, for example, the 5-HT$_{1A}$ (serotonin) binding test as described by Matzen et al., J. Med. Chem. 2000, 43, 1149–57, in particular on page 1156 with reference to Eur. J. Pharmacol., 1987, 140, 143–155.

The agonism of the substances at the 5-HT$_{1A}$ receptor can likewise be tested by the GTPgammaS test as described by Newman-Tancredi et al. (Eur. J. Pharmacol. 1996, 307, 107–11). This test is carried out using membranes of cells which express 5-HT$_{1A}$ receptors on their membrane. The binding of a 5-HT$_{1A}$ receptor agonist to the G-protein-coupled receptor in these cell membranes results in replacement of GDP by GTP on the alpha-subunit of the G-protein. This is followed by dissociation of the G-protein into the alpha-, beta- and gamma-subunits. Whereas GTP is hydrolysed, the non-hydrolysable, radioactively labelled GTP derivative [$^{35}$S]GTPgamma leads to a virtually irreversible complex with the alpha-subunit. The amount of [$^{35}$S]GTP-gammaS bound to the cell membranes can thus be used as an indicator of receptor activation. After incubation, the membrane preparation comprising the receptors is separated from the incubation medium by rapid filtration, and the bound radioactivity is counted.

5-HT reuptake inhibition can also be detected in vivo using microdialysis, which has been described by DiChiara (Trends in Pharmacol. Sci., 1990, 11, 116–121). A physiological solution is passed through a probe implanted in rat brains. The solution takes up neurotransmitters from the brain during passage and is subsequently analysed. Thus, for example, the content of 5-HT in the solution after perfusion is proportional to that in the brain tissue and is increased after administration of a substance having 5-HT reuptake inhibiting properties (Gardier et al., Fundam. Clin. Pharmacol., 1996, 10, 16–27).

Owing to their particular efficacy as combined 5-HT$_{1A}$ agonists and selective 5HT reuptake inhibitors, compounds of the formula I and their physiologically acceptable salts and solvates can be used as medicament active ingredients for anxiolytic, antidepressive, antipsychotic and/or neuroleptic agents.

In particular, they can be employed for the treatment of depression, including the sub-types severe depression and cyclothymic depression, of anxiety states, including the sub-types panic attacks with or without agoraphobia, obsessive-compulsive disorders (OCD)/obsessive-compulsive spectrum disorders (OCSD), specific anxiety disorders, social anxiety disorders, acute stress disorders, post-traumatic stress disorders or generalised anxiety disorders, of psychiatric illnesses, such as psychosis, schizophrenia, schizoaffective psychosis or cyclothymia, Alzheimer's disease, learning disorders, age-dependent memory disorders, of cerebral infarction, such as strokes or cerebral ischaemia, of tension states, of side-effects in the treatment of high blood pressure, for the prophylaxis and therapy of cerebral illnesses, such as migraine, of acromegaly, hypogonadism, secondary amenorrhoea, premenstrual syndrome or undesired puerperal lactation, of pain, sleep disorders, narcolepsy, bipolar illnesses, mania, dementia, addiction disorders, sexual dysfunction, anorexia, eating disorders, obesity or fibromyalgia.

The term "pain" is taken to mean all types of pain, in particular chronic pain states, such as diabetic neuropathy, nervous pain, central nervous and body pain, enteralgia and cancerous pain, inflammatory pain, postoperative pain, chronic back pain, sciatica, throat and neck pain, tension headaches, cluster headaches, chronic daily headaches, herpes neuralgia, neuralgia after herpes, facial and oral neuralgia, pain syndromes of the muscles and fascia, phantom pain, amputation stump pain, paraplegia, dental pain, opiate-resistant pain, postoperative pain, including after heart operations and mastectomies, labour and delivery pain, postnatal pain, post-stroke pain, angina pain, urogenital tract pain, including pelvic pain, cystitis and orchialgia, pain in connection with premenstrual syndrome, pain after burns, injuries by chemicals and after sunburn, and pain in connection with bone injuries.

Compounds of the formula I and their salts and solvates are also suitable as intermediates for the preparation of other medicament active ingredients.

The invention relates to the compounds of the formula I and to their physiologically acceptable acid-addition salts. The invention also relates to the solvates, for example hydrates or alcoholates, of these compounds.

The term solvates of the compounds of the formula I is taken to mean adductions of inert solvent molecules onto the compounds of the formula I which form owing to their mutual attractive force. Solvates are, for example, monohydrates or dihydrates or addition compounds with alcohols, such as, for example, with methanol or ethanol.

The invention relates to the compounds of the formula I and their salts and solvates according to claim 1 and to a process for the preparation of compounds of the formula I and their salts and solvates, characterised in that a) a compound of the formula II

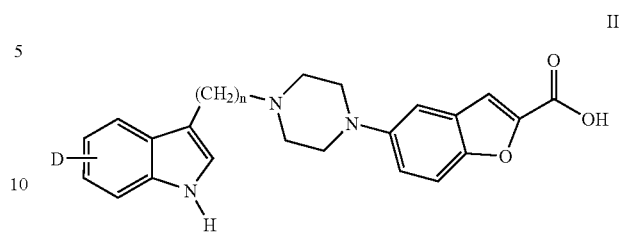

in which D and n are as defined in claim 1, is reacted with a compound of the formula III

or a salt of a compound of the formula III, in which $R^1$ and $R^2$ are as defined in claim 1, or b) a compound of the formula IV

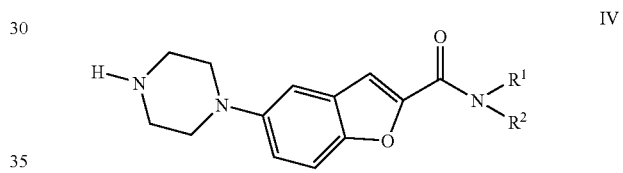

in which $R^1$ and $R^2$ are as defined in claim 1, is reacted with a compound of the formula V

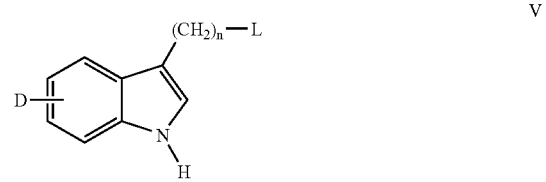

in which L is Cl, Br, I or a free or reactively functionally modified OH group, and D and n are as defined in claim 1, or c) if desired one of the radicals D, $R^1$ and/or $R^2$ is converted into another radical D, $R^1$ and/or $R^2$ by, for example, cleaving an OA group to form an OH group and/or converting a CHO group into a CN group, and/or a resultant base of the formula I is converted into one of its salts by treatment with an acid.

The invention also relates to the compounds of the formula I according to claim 1 and to their physiologically acceptable salts and solvates as medicament active ingredients.

The invention likewise relates to the compounds of the formula I according to claim 1 and to their physiologically acceptable salts or solvates as agonists of the 5-HT$_{1A}$ receptor and selective 5-HT reuptake inhibitors.

For all radicals which occur more than once, such as, for example, A or Hal, their meanings are independent of one another.

The radical A is unbranched or branched alkyl and has from 1 to 6, preferably 1, 2, 3 or 4, in particular 1 or 2, carbon atoms. Alkyl is therefore in particular, for example, methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethyl-butyl, 1-ethyl-1-methylpropyl, 1-ethyl-2-methylpropyl, 1,1,2- or 1,2,2-tri-methylpropyl, in which it is possible for one $CH_2$ group to be replaced by an O or S atom or by a $CH=CH$ group or for at least one H atom to be replaced by F.

The radical A is therefore furthermore, for example, trifluoromethyl, pentafluoroethyl, heptafluoropropyl, methoxymethyl, methoxyethyl, methoxypropyl, ethoxymethyl, ethoxyethyl, ethoxypropyl, methylsulfanylmethyl, methylsulfanylethyl, methylsulfanylpropyl, ethylsulfanylmethyl, ethylsulfanylethyl, ethylsulfanylpropyl, allyl, propenyl, but-2-enyl, but-3-enyl, pent-3-enyl, pent-4-enyl or hex-3-enyl.

A is particularly preferably methyl or tert-butyl, very particularly preferably methyl.

Ar is phenyl, naphthyl or biphenyl, each of which is unsubstituted or mono-substituted or polysubstituted by Hal, A, $OR^4$, $N(R^4)_2$, $NO_2$, CN, $COOR^4$, $CON(R^4)_2$, $NR^4COR^4$, $NR^4CON(R^4)_2$, $NR^4SO_2A$, $COR^4$, $SO_2NR^4$ or $S(O)_mA$, where A has one of the meanings indicated above, and $R^4$ and m have one of the meanings indicated below.

Ar is preferably unsubstituted or substituted phenyl, naphthyl or biphenyl, specifically preferably phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-trifluoromethylphenyl, o-, m- or p-hydroxyphenyl, o-, m- or p-nitrophenyl, o-, m- or p-(trifluoromethoxy)phenyl, o-, m- or p-cyano-phenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-(difluoromethoxy)phenyl, o-, m- or p-(fluoromethoxy) phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromo-phenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2,3,4-, 2,3,5-, 2,3,6-, 2,4,6- or 3,4,5-trichlorophenyl, 2,4,6-tri-tert-butylphenyl, furthermore preferably 2-nitro-4-(trifluoromethyl)phenyl, 3,5-di-(trifluoromethyl)phenyl, 2,5-dimethyl-phenyl, 2-hydroxy-3,5-dichlorophenyl, 2-fluoro-5- or 4-fluoro-3-(trifluoro-methyl) phenyl, 4-chloro-2- or 4-chloro-3-(trifluoromethyl), 2-chloro-4- or 2-chloro-5-(trifluoromethyl)phenyl, 4-bromo-2- or 4-bromo-3-(trifluoro-methyl)phenyl, p-iodophenyl, 2-nitro-4-methoxyphenyl, 2,5-dimethoxy-4-nitrophenyl, 2-methyl-5-nitrophenyl, 2,4-dimethyl-3-nitrophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxy-phenyl, 3-chloro-6-methoxyphenyl, 2-methoxy-5-methylphenyl or 2,4,6-tri-isopropylphenyl.

Ar is particularly preferably phenyl.

Unsubstituted or A-substituted cycloalkyl having from 3 to 10 carbon atoms is preferably cyclopropyl, cyclobutyl, cyclopentyl, cyclohexyl, 4-methyl-cyclohexyl, cycloheptyl or cyclooctyl. Cycloalkyl is likewise monocyclic or bicyclic terpenes, preferably p-menthane, menthol, pinane, bornane or camphor, including each known stereoisomeric form, or adamantyl. For camphor, this means both L-camphor and D-camphor. Cycloalkyl is particularly preferably cyclopropyl, cyclobutyl, cyclopentyl, cyclohexyl, cycloheptyl or 4-methylcyclohexyl.

Hal is fluorine, chlorine, bromine or iodine, in particular chlorine or bromine. In compounds of the formula I, Hal is particularly preferably fluorine.

Het is a saturated, unsaturated or aromatic monocyclic or bicyclic heterocyclic radical having from 5 to 10 ring members, in which from 1 to 4 N and/or from 1 to 4 S and/or from 1 to 4 O atoms may be present, and the heterocyclic radical may be monosubstituted, disubstituted or trisubstituted by Hal, A, $—[C(R^4)_2]_o—Ar$, $—[C(R^4)_2]_o$-cycloalkyl, $OR^4$, $N(R^4)_2$, $NO_2$, CN, $COOR^4$, $CON(R^4)_2$, $NR^4COA$, $NR^4CON(R^4)_2$, $NR^4SO_2A$, $COR^4$, $SO_2NR^4$ or $S(O)_mA$ and/or carbonyl oxygen, where A and cycloalkyl have one of the meanings indicated above, and $R^4$, m and o have one of the meanings indicated below.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, further preferably 1,2,3-triazol-1-, 4- or -5-yl, 1,2,4-triazol-1-, 4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 4- or 5-benzothiadiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or fully hydrogenated. Het may thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6- or -7-1H-indolyl, 2,3-dihydro-1-, -2-, -3-, 4- or -5-pyrazolyl, tetrahydro-1-, -3- or -4-pyrazolyl, 1,4-dihydro-1-, -2-, -3- or -pyridyl, 1,2,3,4-tetrahydro-1-, -2-, -3-, -4-, -5- or -6-pyridyl, 1,2,3,6-tetrahydro-1-, -2-, -3, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or 4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

Het is particularly preferably unsubstituted furan-2-yl, tetrahydrofuran-2-yl, pyridin-4-yl, pyridin-3-yl, pyridin-2- yl, thiophen-2-yl or imidazol-5-yl. Het is likewise preferably pyridin-4-yl, pyridin-2-yl, tert-butoxycarbonylpiperidin-4-yl or piperidin-4-yl.

D is H, OH, OA, CN, Hal, $COR^3$ or $CH_2R^3$, where $R^3$ has one of the meanings indicated below. D is preferably F or CN, particularly preferably CN.

$R^1$ is amino, hydroxyl, cyano, —C(=NR$^4$)—N(R$^4$)$_2$, Het, unsubstituted or A-substituted cycloalkyl having from 3 to 10 carbon atoms, or unbranched or branched alkyl having from 1 to 10 carbon atoms, with the proviso that at least one $CH_2$ group in the alkyl group has been replaced by an O or S atom, by a CH=CH group or by a C≡C group, or with the proviso that at least one hydrogen atom in the alkyl group has been replaced by Hal, OH, Ar, Het, cycloalkyl having from 3 to 10 carbon atoms, $N(R^4)_2$, CN, $COOR^4$, $CON(R^4)_2$, $NR^4COR^4$, $NR^4COOR^4$, $NR^4CON(R^4)_2$, $NR^4SO_2A$ or $SO_2NR^4$, where A, Ar, Hal, Het and cycloalkyl have one of the meanings indicated above, and $R^4$ has one of the meanings indicated below.

$R^1$ is preferably Het, unsubstituted or A-substituted cycloalkyl having from 3 to 7 carbon atoms, or unbranched alkyl having from 1 to 6 carbon atoms, with the proviso that at least one $CH_2$ group in the alkyl group has been replaced by an O atom, by a CH=CH group or by a C≡C group, or with the proviso that at least one hydrogen atom in the alkyl group has been replaced by Hal, OH, Ar, Het, cycloalkyl having from 3 to 10 carbon atoms, $N(R^4)_2$, $NR^4COOR^4$, CN or $CON(R^4)_2$, where A, Ar, Hal, Het and cycloalkyl have one of the meanings indicated above, and $R^4$ has one of the meanings indicated below.

$R^1$ is particularly preferably allyl, benzyl, phenylethyl, 2-methoxyethyl, 3-methoxypropyl, 3-ethoxypropyl, aminocarbonylmethyl, 2-aminomethyl, 2-dimethylaminoethyl, 2-diethylaminoethyl, 3-dimethylaminopropyl, 4-dimethylaminobutyl, 2-methylaminoethyl, cyanomethyl, 2,2,2-trifluoroethyl, 2-hydroxyethyl, 3-hydroxypropyl, prop-2-inyl, 2-(tert-butoxycarbonyl-methylamino)ethyl, 2-tert-butoxycarbonylaminoethyl, cyclopropyl, cyclobutyl, cyclopentyl, cyclohexyl, cycloheptyl, 4-methylcyclohexyl, cyclohexylmethyl, furan-2-ylmethyl, 2-morpholin-4-ylethyl, pyridin-3-ylmethyl, pyridin-2-ylmethyl, pyridin-4-ylmethyl, 2-imidazol-5-ylethyl, thiophen-2-ylmethyl, tetrahydrofuran-2-ylmethyl, piperidin-4-ylmethyl, piperidin-4-yl, tert-butoxycarbonylpiperidin-4-ylmethyl, tert-butoxycarbonylpiperidin-4-yl, pyridin-4-yl, pyridin-2-yl, amino, cyano or hydroxyl. $R^1$ is particularly preferably 2-aminoethyl, 2-methylaminoethyl, piperidin-4-ylmethyl or piperidin-4-yl.

$R^2$ is H, A or $R^1$, where A and $R^1$ have one of the meanings indicated above. $R^2$ is particularly preferably H or methyl.

$NR^1R^2$ together is a three- to 7-membered saturated heterocyclic ring, in which, in addition, 1 or 2 N and/or 1 or 2 S and/or 1 or 2 O atoms and/or one $S(O)_m$ group may be present and which may be substituted by A, Hal, cycloalkyl having from 3 to 10 carbon atoms, $OR^4$, $N(R^4)_2$, CN, $COOR^4$, $CON(R^4)_2$, $NR^4COR^4$ and/or carbonyl oxygen, where A, Hal, cycloalkyl and $R^4$ have one of the meanings indicated above, and m has on of the meanings indicated below.

$NR^1R^2$ is preferably 1-, 2- or 3-pyrrolidinyl, tetrahydro-1-, -2- or -4-imidazolyl, tetrahydro-1-, -3- or -4-pyrazolyl, 1-, 2-, 3- or 4-piperidinyl, 1-, 2-, 3- or 4-azepanyl, 2-, 3- or 4-morpholinyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 4-tert-butoxycarbonylpiperazin-1-yl, 4-methylpiperazin-1-yl or 4-oxopiperazin-1-yl.

$NR^1R^2$ is particularly preferably piperidin-1-yl or morpholin-1-yl.

$R^3$ is OH, OA or $N(R^4)_2$, where A has one of the meanings indicated above, and $R^4$ has one of the meanings indicated below.

$R^4$ is H or A, where A has one of the meanings indicated above.

n is 2, 3, 4 or 5, particularly preferably 4.

m is 1 or 2.

o is 0, 1, 2, 3 or 4.

Accordingly, the invention relates, in particular, to the compounds of the formula I in which at least one of the said radicals has one of the preferred meanings indicated above. Some preferred groups of compounds may be expressed by the following sub-formulae Ia to Ih, which conform to the formula I and in which the radicals not designated in greater detail have the meaning indicated for the formula I, but in which in Ia D is CN;

in Ib n is 4;

in Ic D is CN and
 n is 4;

in Id $R^1$ is amino, hydroxyl, cyano, —C(=NR$^4$)—N(R$^4$)$_2$, Het, unsubstituted or A-substituted cycloalkyl having from 3 to 7 carbon atoms, or unbranched alkyl having from 1 to 6 carbon atoms, with the proviso that at least one $CH_2$ group in the alkyl group has been replaced by an O atom, by a CH=CH group or by a C≡C group, or with the proviso that at least one hydrogen atom in the alkyl group has been replaced by Hal, OH, Ar, Het, cycloalkyl having from 3 to 10 carbon atoms, $N(R^4)_2$, $NR^4COOR^4$, CN or $CON(R^4)_2$;

in Ie D is CN,
 n is 4,
 $R^1$ is Het, unsubstituted or A-substituted cycloalkyl having from 3 to 7 carbon atoms, or unbranched alkyl having from 1 to 6 carbon atoms, with the proviso that at least one $CH_2$ group in the alkyl group has been replaced by an O atom, by a CH=CH group or by a C≡C group, or with the proviso that at least one hydrogen atom in the alkyl group has been replaced by Hal, OH, Ar, Het, cycloalkyl having from 3 to 10 carbon atoms, $N(R^4)_2$, $NR^4COOR^4$, CN or $CON(R^4)_2$;

in If $NR^1R^2$ together form a three- to 7-membered saturated heterocyclic ring which is unsubstituted or substituted by carbonyl oxygen, A or $COOR^4$, where 1 O atom may additionally be present;

in Ig D is CN,
 n is 4, and
 $NR^1R^2$ together form a three- to 7-membered saturated heterocyclic ring which is unsubstituted or substituted by carbonyl oxygen, A or $COOR^4$, where, in addition, 1 O atom may be present;

in Ih D is CN,
 n is 4,
 $R^2$ is H or A, and
 $R^1$ is unsubstituted or A-substituted cycloalkyl having from 3 to 7 carbon atoms, or unbranched alkyl having from 1 to 6 carbon atoms, with the proviso that at least one $CH_2$ group in the alkyl group has been replaced by an O atom, by a CH=CH group or by a C≡C group, or with the proviso that at least one hydrogen atom in the alkyl group has been replaced by Hal, OH, Ar, Het, cycloalkyl having from 3 to 10 carbon atoms, $N(R^4)_2$, $NR^4COOR^4$, CN or $CON(R^4)_2$, or NR$^1$R$^2$ together form a three- to 7-membered saturated heterocyclic ring which is unsubstituted or substituted by carbonyl oxygen, A or COOR$^4$, where, in addition, 1 O atom may be present.

The invention relates, in particular, to the compounds
a) N-(2-methoxyethyl)-5-{4-[4-(5-cyano-1H-indol-3-yl)butyl]piperazin-1-yl}benzofuran-2-carboxamide,
b) N-carbamoylmethyl-5-{4-[4-(5-cyano-1H-indol-3-yl)butyl]piperazin-1-yl}benzofuran-2-carboxamide,
c) N-(2-hydroxyethyl)-5-{4-[4-(5-cyano-1H-indol-3-yl)butyl]piperazin-1-yl}benzofuran-2-carboxamide,
d) N-(pyridin-2-ylmethyl)-5-{4-[4-(5-cyano-1H-indol-3-yl)butyl]piperazin-1-yl}benzofuran-2-carboxamide,
e) N-(pyridin-4-ylmethyl)-5-{4-[4(5-cyano-1H-indol-3-yl)butyl]piperazin-1-yl}benzofuran-2-carboxamide or
f) N-(2-methylaminoethyl)-5-{4-[4-(5-cyano-1H-indol-3-yl)butyl]piperazin-1-yl}benzofuran-2-carboxamide, and their salts and solvates.

Very particularly preferred compounds are
f) N-(2-methylaminoethyl)-5-{4-[4-(5-cyano-1H-indol-3-yl)butyl]piperazin-1-yl}benzofuran-2-carboxamide;
g) N-(2-aminoethyl)-5-{4-[4-(5-cyano-1H-indol-3-yl)butyl]piperazin-1-yl}benzofuran-2-carboxamide;
h) N-(2-aminoethylmethy)-5-{4-[4-(5-cyano-1H-indol-3-yl)butyl]piperazin-1-yl}benzofuran-2-carboxamide;
i) N-(2-methylaminoethylmethyl)-5-{4-[4-(5-cyano-1H-indol-3-yl)butyl]-piperazin-1-yl}benzofuran-2-carboxamide;
j) N-(piperidin-4-ylmethyl)-5-{4-[4-(5-cyano-1H-indol-3-yl)butyl]piperazin-1-yl}benzofuran-2-carboxamide or
k) N-piperidin-4-yl-5-{4-[4-(5-cyano-1H-indol-3-yl)butyl]piperazin-1-yl}benzofuran-2-carboxamide, and their salts and solvates.

The compounds of the formula I and also the starting materials for their preparation are, in addition, prepared by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula I. On the other hand, it is possible to carry out the reaction stepwise.

In the compounds of the formulae V and VI, the radical L is preferably Cl or Br; however, it may also be I, OH or also preferably a reactively functionally modified OH group, in particular alkylsulfonyloxy having 1-6 (for example methanesulfonyloxy) or arylsulfonyloxy having 6-10 carbon atoms (for example benzenesulfonyloxy, p-toluenesulfonyloxy or 1- or 2-naphthalenesulfonyloxy), or alternatively trichloromethoxy, alkoxy, such as, for example, methoxy, ethoxy, propoxy or butoxy, furthermore also phenoxy.

The compounds of the formula I can preferably be obtained by reacting compounds of the formula II with compounds of the formula III. The starting materials of the formula II are generally known; the compounds of the formula II which are not known can easily be prepared analogously to the known compounds, in particular by the procedures of Examples 1 to 10 of U.S. Pat. Nos. 5,532,241. 5,532,241 is incorporated herein by way of reference.

Amines of the formula III are commercially available or can easily be prepared analogously to the known amines.

The reaction of the compounds II and III is carried out by methods which are known from the literature for the acylation of amines [Houben-Weyl, l.c., Volume 15/II, pages 1 to 806 (1974)]. However, it is also possible to react the compounds in the presence of an inert solvent. Examples of suitable inert solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, if desired also mixtures of these solvents with one another or mixtures with water. The addition of an acid-binding agent, for example an alkali or alkaline earth metal hydroxide, carbonate or bicarbonate, or another salt of a weak acid of the alkali or alkaline earth metals, preferably of potassium, sodium or calcium, or the addition of an organic base, such as triethylamine, dimethylaniline, pyridine, 4-dimethylaminopyridine, quinoline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), may be favourable. The reaction temperature is between about −10° and 150°, normally between 0° and 130°, preferably between 0° and 30°, depending on the conditions used.

The reaction time is between a few minutes and a number of days, depending on the conditions used.

Instead of the carboxylic acid of the formula II, it is also possible to use derivatives of this acid, preferably the pre-activated carboxylic acid, or a corresponding carboxylic acid halide, a symmetrical or mixed anhydride or an active ester of the acid of the formula II. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

The coupling reaction, i.e. the acylation, preferably proceeds in the presence of a dehydrating agent, for example a carbodiimide, such as dicyclohexylcarbodiimide (DCC), N-(3-dimethylaminopropyl)-N'-ethyl-carbodiimide hydrochloride (EDC) or diisopropylcarbodiimide (DIC), furthermore, for example, propanephosphonic anhydride (cf. Angew. Chem. 1980, 92, 129), diphenylphosphoryl azide or 2-ethoxy-N-ethoxycarbonyl-1,2-dihydroquinoline.

It is furthermore possible to prepare compounds of the formula I by reacting amines of the formula IV with a component of the formula V. The reaction conditions for acylations of amines, as described above, apply.

Compounds of the formula IV can be prepared, for example, by reaction of the free acid of the compound of the formula IV (compounds of the formula IV-A), which can be prepared, for example, in accordance with the teaching of EP 0 738 722 or of WO 01/04112, with an amine of the formula III under the above-mentioned reaction conditions. EP 0 738 722 is hereby incorporated as reference. WO 01/04112 is hereby incorporated as reference.

Free acids of the formula IV (formula IV-A)

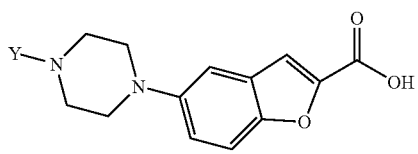

in which
Y is H, benzyl or another amino-protecting group, and/or salts thereof can be obtained by the following reaction:
(1) 3-R-6-hydroxybenzaldehyde, in which R is Cl, Br or I, is reacted with a compound of the formula VI

L-CH$_2$—CO-Q    VI in which L is Cl, Br, I or a free or functionally modified OH group,
Q is OR", and
R" is alkyl having 1–6 carbon atoms, to give a compound of the formula VII

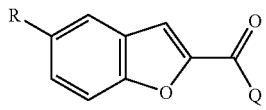

in which
R is Cl, Br or I, and Q is as defined under the formula VI,
(2) the compound of the formula VII is reacted, with transition-metal catalysis, with a compound of the formula VIII 4-Y-piperazine    VIII in which
Y is benzyl or another amino-protecting group, and the ester is cleaved by basic saponification.

The amino-protecting group can be cleaved off under reaction conditions which are known for the protecting group. The transition-metal-catalysed amination takes place under the reaction conditions known to the person skilled in the art, in particular under the conditions of Example 5 of WO 01/04112.

The amino-protecting group on the piperazine ring of the compound of the formula IV-A is preferably cleaved off after the reaction with an amine of the formula III to give the compound of the formula IV.

Free acids of the formula IV (formula IV-A) in which Y is as defined above can likewise be obtained in accordance with the teaching of Examples 1 to 3 of EP 0 738 722, combined with saponification of an ester. The conditions for the ester cleavage or saponification are known and familiar to the person skilled in the art.

Compounds of the formula V are commercially available or are known from EP 0 496 222. EP 0 496 222 is hereby incorporated as reference. In accordance with the teaching of EP 0 496 222, Examples 1 to 3, the indole derivatives of the formula V in which L=OH can be obtained, for example, by reduction of the corresponding carboxylic acid or esters thereof. Treatment with thionyl chloride, hydrogen bromide, phosphorus tribromide or similar halogen compounds gives the corresponding halides of the formula V. The corresponding sulfonyloxy compounds are obtainable from the primary alcohols of the formula V by reaction with the corresponding sulfonic acid chlorides.

Compounds of the formula I can likewise be prepared by reaction of a compound of the formula IX

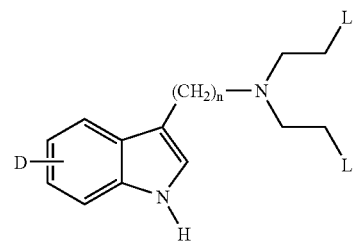

in which
D and n are as defined in claim 1, and
L is Cl, Br, I or a free or functionally modified OH group, with a compound of the formula X

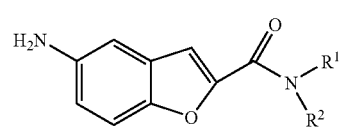

in which R$^1$ and R$^2$ are as defined in claim 1. The reaction conditions are known from EP 0 496 222, Example 10. It is likewise possible to protect the indole nitrogen by means of an amino-protecting group, as described above, before the reaction with a compound of the formula X, and, when the reaction is complete, to remove the protecting group again under the known reaction conditions for the selected protecting group.

A resultant base of the formula I can be converted into the associated acid-addition salt using an acid. Suitable acids for this reaction are those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid or sulfamic acid, furthermore organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

If desired, the free bases of the formula I can be liberated from their salts by treatment with strong bases, such as sodium hydroxide, potassium hydroxide, sodium carbonate or potassium carbonate, so long as no further acidic groups are present in the molecule. In the cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

The invention furthermore relates to the medicament active ingredients according to the invention having a 5-$HT_{1A}$ receptor agonistic and 5-HT reuptake inhibiting action for the treatment of depression, anxiety states, panic attacks, obsessive-compulsive disorders, psychiatric illnesses, cerebral infarction, cerebral ischaemia, tension states, side-effects in the treatment of high blood pressure, for the prophylaxis and therapy of cerebral illnesses, acromegaly, hypogonadism, secondary amenorrhoea, premenstrual syndrome, undesired puerperal lactation, pain, sleep disorders, narcolepsy, bipolar illnesses, mania, dementia, addiction illnesses, sexual dysfunction, eating disorders, obesity or fibromyalgia.

The invention furthermore relates to pharmaceutical preparations comprising at least one compound of the formula I and/or one of its physiologically acceptable salts or solvates. The compounds of the formula I can be converted into a suitable dosage form here together with at least one solid, liquid and/or semi-liquid excipient or assistant and, if desired, in combination with one or more further active ingredients.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Particularly suitable for oral use are tablets, pills, coated tablets, capsules, powders, granules, syrups, juices or drops, suitable for rectal use are suppositories, suitable for parenteral use are solutions, preferably oil-based or aqueous-solutions, furthermore suspensions, emulsions or implants, and suitable for topical use are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

The substances according to the invention are generally administered analogously to commercial preparations (for example citalopram), preferably in doses of between about 0.1 and 500 mg, in particular between 0.2 and 50 mg per dosage unit. The daily dose is preferably between about 0.001 and 10 mg/kg of body weight. The low doses (from about 0.2 to 1 mg per dosage unit; from about 0.001 to 0.005 mg/kg of body weight) are suitable, in particular, for use as migraine agents; for the other indications, doses of between 10 and 50 mg per dosage unit are preferred. However, the specific dose for each particular patient depends on a very wide variety of factors, for example on the efficacy of the specific compound employed, on the age, body weight, general state of health, sex, on the diet, on the time and method of administration, on the excretion rate, medicament combination and severity of the particular disorder to which the therapy applies. Oral administration is preferred.

The invention furthermore relates to the use of the compounds according to the invention and/or of their physiologically acceptable salts and solvates for the preparation of a medicament, in particular a medicament having a 5-$HT_{1A}$ receptor agonistic and 5-HT reuptake inhibiting action.

The invention also relates to the use of the compounds according to the invention and/or of their physiologically acceptable salts and solvates for the preparation of a medicament having a 5-$HT_{1A}$ receptor agonistic and 5-HT reuptake inhibiting action for the treatment of depression, anxiety states, panic attacks, obsessive-compulsive disorders, psychiatric illnesses, cerebral infarction, cerebral ischaemia, tension states, side-effects in the treatment of high blood pressure, for the prophylaxis and therapy of cerebral illnesses, acromegaly, hypogonadism, secondary amenorrhoea, premenstrual syndrome, undesired puerperal lactation, pain, sleep disorders, narcolepsy, bipolar illnesses, mania, dementia, addiction illnesses, sexual dysfunction, eating disorders, obesity or fibromyalgia.

Even without further details, it is assumed that a person skilled in the art will be able to utilise the above description in the broadest scope. The preferred embodiments should therefore merely be regarded as descriptive disclosure which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation. The purified compounds are, if desired, freeze-dried.

Mass spectrometry (MS): ESI (electrospray ionisation) $(M+H)^+$

EXAMPLE 1

0.1 ml (0.91 mmol) of 4-methylmorpholine is added to a solution of 200 mg (0.452 mmol) of 5-{4-[4-(5-cyano-1H-indol-3-yl)butyl]piperazin-1-yl}benzofuran-2-carboxylic acid, 50.0 mg (0.452 mmol) of 2-aminoacetamide hydrochloride, 87.0 mg (0.452 mmol) of N-(3-dimethylaminopropyl)-N'-ethyl-carbodiimide hydrochloride (EDC) and 61.0 mg (0.452 mmol) of hydroxy-benzotriazole hydrate (HOBt) in 2 ml of dimethylformamide (DMF), and the mixture is stirred at room temperature for 18 hours. The reaction mixture is added to water, and the precipitate is filtered off, giving N-carbamoyl-methyl-5-{4-[4-(5-cyano-1H-indol-3-yl) )butyl]piperazin-1-yl}benzofuran-2-carboxamide; ESI 499.

Reaction of the free base with 1N HCl solution in isopropanol gives N-carbamoylmethyl-5-{4-[4-(5-cyano-1H-indol-3-yl)butyl]piperazin-1-yl}benzofuran-2-carboxamide hydrochloride.

EXAMPLE 2

Analogously to Example 1, reaction of 5-{4-[4-(5-cyano-1H-indol-3-yl)butyl]-piperazin-1-yl}benzofuran-2-carboxylic acid with
morpholine gives
3-(4-{4-[2-(morpholine-4-carbonyl)benzofuran-5-yl]piperazin-1-yl}butyl)-1H-indole 5-carbonitrile; m.p. 261–263°;

piperidine hydrochloride gives
3-(4-{4-[2-(piperidine-1-carbonyl)benzofuran-5-yl]piperazin-1-yl}butyl)-1H-indole 5-carbonitrile; m.p. 157–159°;

benzylamine gives
N-benzyl-5-{4-[4-(5-cyano-1H-indol-3-yl)butyl]piperazin-1-yl}benzofuran-2-carboxamide; ESI 532;

2-methoxyethylamine gives
N-(2-methoxyethyl)-5-{4-[4-(5-cyano-1H-indol-3-yl)butyl]piperazin-1-yl}benzofuran-2-carboxamide; ESI 500; reaction of the free base with 1N HCl solution in isopropanol gives N-(2-methoxyethyl)-5-{4-[4-(5-cyano-1H-indol-3-yl)butyl]piperazin-1-yl}benzofuran-2-carboxamide hydrochloride;

3-methoxypropylamine gives
N-(3-methoxypropyl)-5-{4-[4-(5-cyano-1H-indol-3-yl)butyl]piperazin-1-yl) benzofuran-2-carboxamide; ESI 514;

allylamine gives
N-allyl-5-{-4-[4-(5-cyano-1H-indol-3-yl)butyl]piperazin-1-yl}benzofuran-2-carboxamide; ESI 482;

cyclohexylamine gives
N-cyclohexyl-5-{4-[4-(5-cyano-1H-indol-3-yl)butyl]piperazin-1-yl}benzofuran-2-carboxamide; ESI 524;

$N^1,N^1$-dimethylethane-1,2-diamine gives
N-(2-dimethylaminoethyl)-5-{4-[4-(5-cyano-1H-indol-3-yl)butyl]piperazin-1-yl}benzofuran-2-carboxamide; ESI 513;

C-furan-2-ylmethylamine gives
N-(furan-2-ylmethyl)-5-{4-[4-(5-cyano-1H-indol-3-yl)butyl]piperazin-1-yl}benzofuran -2-carboxamide; ESI 522;

cyclopropylamine gives
N-cyclopropyl-5-{4-[4-(5-cyano-1H-indol-3-yl)butyl]piperazin-1-yl}benzofuran-2-carboxamide; ESI 482;

cyclopentylamine gives
N-cyclopentyl-5-{4-[4-(5-cyano-1H-indol-3-yl)butyl]piperazin-1-yl}benzofuran-2-carboxamide; ESI 510;

aminoacetonitrile gives
N-cyanomethyl-5-{4-[4-(5-cyano-1H-indol-3-yl)butyl]piperazin-1-yl}benzofuran-2-carboxamide; ESI 481;

2,2,2-trifluoroethylamine gives
N-(2,2,2-trifluoroethyl)-5-{4-[4-(5-cyano-1H-indol-3-yl)butyl]piperazin-1-yl}benzofuran-2-carboxamide; ESI 524;

Prop-2-ynylamine Gives
N-prop-2-ynyl-5-{4-[4-(5-cyano-1H-indol-3-yl)butyl]piperazin-1-yl}benzofuran-2-carboxamide; ESI 480;

cyclobutylamine gives
N-cyclobutyl-5-{4-[4-(5-cyano-1H-indol-3-yl)butyl]piperazin-1-yl}benzofuran-2-carboxamide; ESI 496; reaction of the free base with 1N HCl solution in isopropanol gives N-cyclobutyl-5-{4-[4-(5-cyano-1H-indol-3-yl)-butyl]piperazin-1-yl}benzofuran-2-carboxamide hydrochloride;

phenethylamine gives
N-phenethyl-5-{4-[4-(5-cyano-1H-indol-3-yl)butyl]piperazin-1-yl}benzofuran-2-carboxamide; ESI 546;

2-morpholin-4-ylethylamine gives
N-(2-morpholin-4-ylethyl)-5-{4-[4-(5-cyano-1H-indol-3-yl)butyl]piperazin-1-yl}benzofuran-2-carboxamide; ESI 555;

2-aminoethanol gives
N-(2-hydroxyethyl)-5-{4-[4-(5-cyano-1H-indol-3-yl)butyl]piperazin-1-yl}benzofuran-2-carboxamide; ESI 486; reaction of the free base with 1N HCl solution in isopropanol gives N-(2-hydroxyethyl)-5-{4-[4-(5-cyano-1H-indol-3-yl)butyl]piperazin-1-yl}benzofuran-2-carboxamide hydrochloride;

3-aminopropanol gives
N-(3-hydroxypropyl)-5-{4-[4-(5-cyano-1H-indol-3-yl)butyl]piperazin-1-yl}benzofuran -2-carboxamide; ESI 500;

$N^1,N^1$-diethylethane-1,2-diamine gives
N-(2-diethylaminoethyl)-5-{4-[4-(5-cyano-1H-indol-3-yl)butyl]piperazin-1-yl}benzofuran -2-carboxamide; ESI 541;

$N^1,N^1$-dimethylpropane-1,3-diamine gives
N-(3-dimethylaminopropyl)-5-{4-[4-(5-cyano-1H-indol-3-yl)butyl]piperazin-1-yl}benzofuran-2-carboxamide; ESI 527;

C-pyridin-3-ylmethylamine gives
N-(pyridin-3-ylmethyl)-5-{4-[4-(5-cyano-1H-indol-3-yl)butyl]piperazin-1-yl}benzofuran -2-carboxamide; ESI 533;

C-pyridin-2-ylmethylamine gives
N-(pyridin-2-ylmethyl)-5-{4-[4-(5-cyano-1H-indol-3-yl)butyl]piperazin-1-yl}benzofuran-2-carboxamide; ESI 533; reaction of the free base with 1N HCl solution in isopropanol gives N-(pyridin-2-ylmethyl)-5-{4-[4-(5-cyano-1H-indol-3-yl)butyl]piperazin-1-yl}benzofuran-2-carboxamide hydrochloride;

C-pyridin-4-ylmethylamine gives
N-(pyridin-4-ylmethyl)-5-{4-[4-(5-cyano-1H-indol-3-yl)butyl]piperazin-1-yl}benzofuran-2-carboxamide; ESI 533; reaction of the free base with 1N HCl solution in isopropanol gives N-(pyridin-4-ylmethyl)-5-{4-[4-(5-cyano-1H-indol-3-yl)butyl]piperazin-1-yl}benzofuran-2-carboxamide hydrochloride;

2-(1H-imidazol-4-yl)ethylamine hydrochloride gives
N-[2-(1H-imidazol-4-yl)ethyl]-5-{4-[4-(5-cyano-1H-indol-3-yl)butyl]piperazin-1-yl}benzofuran-2-carboxamide; ESI 536;

C-thiophen-2-ylmethylamine gives
N-(thiophen-2-ylmethyl)-5-{4-[4-(5-cyano-1H-indol-3-yl)butyl]piperazin-1-yl}benzofuran-2-carboxamide; ESI 538;

C-(tetrahydrofuran-2-yl)methylamine gives
N-(tetrahydrofuran-2-ylmethyl)-5-{4-[4-(5-cyano-1H-indol-3-yl)butyl]-piperazin-1-yl}benzofuran-2-carboxamide; ESI 526;

$N^1,N^1$-dimethylbutane-1,4-diamine gives
N-(4-dimethylaminobutyl)-5-{4-[4-(5-cyano-1H-indol-3-yl)butyl]piperazin-1-yl}benzofuran-2-carboxamide; ESI 541;

cycloheptylamine gives
N-cycloheptyl-5-{4-[4-(5-cyano-1H-indol-3-yl)butyl]piperazin-1-yl}benzofuran-2-carboxamide; ESI 538;

3-ethoxypropylamine gives
N-(3-ethoxypropyl)-5-{4-[4-(5-cyano-1H-indol-3-yl)butyl]piperazin-1-yl}benzofuran -2-carboxamide; ESI 528;

$N^1$-methylethane-1,2-diamine gives
N-(2-methylaminoethyl)-5-{4-[4-(5-cyano-1H-indol-3-yl)butyl]piperazin-1-yl}benzofuran -2-carboxamide; ESI 499; reaction of the free base with 1N HCl solution in isopropanol gives N-(2-methylaminoethyl)-5-{4-[4-(5-cyano-1H-indol-3-yl)butyl]piperazin-1-yl}benzofuran-2-carboxamide trihydrochloride; m.p. >233°;

5 cyclohexylmethylamine gives
N-cyclohexylmethyl-5-{4-[4-(5-cyano-1H-indol-3-yl)butylpiperazin-1-yl}benzofuran-2-carboxamide; ESI 538 or 4-methylcyclohexylamine gives
N-(4-methylcyclohexyl)-5-{4-[4-(5-cyano-1H-indol-3-yl)butyl]piperazin-1-yl}benzofuran-2-carboxamide; ESI 538.

EXAMPLE 3

Analogously to Example 1, reaction of 5-{4-[4-(5-cyano-1H-indol-3-yl)butyl]-piperazin-1-yl}benzofuran-2-carboxylic acid with
tert-butyl (2-aminoethyl)carbamate gives
tert-butyl (2-{[1-(5-{4-[4-(5-cyano-1H-indol-3-yl)butyl]piperazin-1-yl}benzofuran-2-yl)methanoyl]amino}ethyl)carbamate, m.p. 209-210°. Removal of the protecting group gives
N-(2-aminoethyl)-5-{4-4-(5-cyano-1H-indol-3-yl)butyl]piperazin-1-yl}benzofuran-2-carboxamide.
Salt formation by reaction of the free base with 1N HCl solution in iso-propanol gives N-(2-aminoethyl)-5-{4-[4-(5-cyano-1H-indol-3-yl)butyl]-piperazin-1-yl}benzofuran-2-carboxamide trihydrochloride, m.p. >144°;
tert-butyl (2-methylaminoethyl)carbamate gives
tert-butyl {2-[(5-4-[4-(5-cyano-1H-indol-2-yl)butyl]piperazin-1-yl}benzofuran -2-carbonyl)methylamino]ethyl}carbamate, and removal of the protecting group gives
N-(2-aminoethyl)methyl-5-{4-[4-(5-cyano-1H-indol-3-yl)butyl]piperazin-1-yl}benzofuran-2-carboxamide.
Reaction of the free base with 1N HCl solution in isopropanol gives N-(2-aminoethyl)methyl-5-{4-[4(5-cyano-1H-indol-3-yl)butyl]piperazin-1-yl}benzofuran-2-carboxamide trihydrochloride, m.p. 212–213°;
$N^1,N^1$-dimethylethane-1,2-diamine gives
N-(2-dimethylaminoethyl)-5-{4-[4-(5-cyano-1H-indol-3-yl)butyl]piperazin-1-yl}benzofuran-2-carboxamide.
Reaction of the free base with 1N HCl solution in isopropanol gives N-(2-dimethylaminoethyl)-5-{4-[4(5-cyano-1H-indol-3-yl)butyl]piperazin-1-yl}benzofuran-2-carboxamide, trihydrochloride, m.p. 224–225';
$N^1,N^2$-dimethylethane-1,2-diamine gives
N-methyl-(2-methylaminoethyl)-5-{4-[4(5-cyano-1H-indol-3-yl)butyl]piperazin-1-yl}benzofuran-2-carboxamide. Reaction of the free base with 1N HCl Solution in isopropanol gives
N-methyl-(2-methylaminoethyl)-5-{4-[4-(5-cyano-1H-indol-3-yl)butyl]piperazin-1-yl}benzofuran-2-carboxamide, trihydrochloride, m.p. 230–233°;
N,N,N'-trimethylethane-1,2-diamine gives
N-(2-dimethylaminoethyl)methyl-5-{4-[4-(5-cyano-1H-indol-3-yl)butyl]piperazin-1-yl}benzofuran-2-carboxamide. Reaction of the free base with 1N HCl solution in isopropanol gives N-(2-dimethylaminoethyl)methyl-5-{4-[4-(5-cyano-1H-indol-3-yl)butyl]piperazin-1-yl}benzofuran-2-carboxamide, trihydrochloride, m.p. 241–242°;
tert-butyl methyl-(2-methylaminoethyl)carbamate gives
dimethylethyl (2-{[1-(5-{4-[4-(5-cyano-1H-indol-3-yl)butyl]piperazin-1-yl}benzofuran-2-yl)methanoyl]amino}ethyl)methylcarbamate;
$N^1,N^1$-dimethylpropane-1,3-diamine gives
N-(3-dimethylaminopropyl)-5-{4-[4-(5-cyano-1H-indol-3-yl)buty]piperazin-1-yl}benzofuran-2-carboxamide. Reaction of the free base with 1N HCl solution in isopropanol gives N-(3-dimethylaminopropyl)-5-{4-[4-(5-cyano1-H-indol-3-yl)butyl]piperazin-1-yl}benzofuran-2-carboxamide, trihydrochloride, m.p. 270–275°;
tert-butyl 4-aminomethylpiperidine-1-carboxylate gives
tert-butyl 4-({[1-(5-{4-[4-(5-cyano-1H-indol-3-yl)butyl]piperazin-1-yl}benzofuran -2-yl)methanoyl]amino}methyl)piperidine-1-carboxylate. Reaction with 1N HCl solution gives
tert-butyl 4-({[1-(5-{4-[4-(5-cyano-1H-indol-3-yl)butyl]piperazin-1-yl}benzofuran-2-yl)methanoyl]amino}methyl)piperidine-1-carboxylate dihydro-chloride, m.p. 205°.
Removal of the Protecting Group gives
N-(piperidin-4-ylmethyl)-5-{4-[4-(5-cyano-1H-indol-3-yl)butyl]piperazin-1-yl}benzofuran-2-carboxamide. Reaction of the free base with 1N HCl solution in isopropanol gives N-(piperidin-4-ylmethyl)-5-{4-[4-(5-cyano-1H-indol-3-yl)butyl]piperazin-1-yl}benzofuran-2-carboxamide, trihydrochloride, m.p. 244–228°;
tert-butyl 4-aminopiperidine-1-carboxylate gives
tert-butyl 4-{[1-(5-{4-[4-(5-cyano-1H-indol-3-yl)butyl]piperazin-1-yl}benzofuran -2-yl)methanoyl]amino}piperidine-1-carboxylate. Reaction with 1N HCl solution gives
tert-butyl 4-{[1-(5-{4-[4-(5-cyano-1H-indol-3-yl)butyl]piperazin-1-yl}benzofuran-2-yl)methanoyl]amino}piperidine-1-carboxylate, dihydrochloride, m.p. 203–205°.
Removal of the Protecting Group gives
N-piperidin-4-yl-5-{4-[4-(5-cyano-1H-indol-3-yl)butyl]piperazin-1-yl}benzofuran-2-carboxamide. Reaction of the free base with 1N HCl solution in isopropanol gives N-piperidin-4-yl-5-{4-[4-(5-cyano-1H-indol-3-yl)butyl]piperazin-1-yl}benzofuran-2-carboxamide, trihydrochloride, m.p. 195°;
pyridin4-ylamine gives
N-pyridin4-yl-5-{4-[4-(5-cyano-1H-indol-3-yl)butyl]piperazin-1-yl}benzofuran-2-carboxamide. Reaction of the free base with 1N HCl solution in isopropanol gives N-pyridin-4-yl-5-{4-[4-(5-cyano-1H-indol-3-yl)butyl]piperazin-1-yl}benzofuran-2-carboxamide, trihydrochloride, m.p. 220°;
pyridin-2-ylamine gives
N-pyridin-2-yl-5-{4-[4-(5-cyano-1H-indol-3-yl)butyl]piperazin-1-yl}benzofuran-2-carboxamide. Reaction of the free base with 1N HCl solution in isopropanol gives N-pyridin-2-yl-5-{4-[4-(5-cyano-1H-indol-3-yl)butyl]piperazin-1-yl}benzofuran-2-carboxamide, dihydrochloride, m.p. 163–170° or N-pyridin-2-yl-5-{4-[4-(5-cyano-1H-indol-3-yl)butyl]piperazin-1-yl}benzofuran-2-carboxamide, trihydrochloride, m.p. 240–245°;
piperidin-4-one gives
3-[4-(4-{2-[1-(4-oxopiperidin-1-yl)methanoyl]benzofuran-5-yl}piperazin-1-yl)butyl]-1H-indole-5-carbonitrile.
Reaction of the free base with 1N HCl solution in isopropanol gives 3-[4-(4-{2-[1-(4-oxopiperidin-1-yl)methanoyl]-benzofuran-5-yl}piperazin-1-yl)butyl]-1H-indole-5-carbonitrile, dihydro-chloride, m.p. >229°;
tert-butyl piperazin-1-carboxylate gives
tert-butyl 4-[1-(5-{4-[4-(5-cyano-1H-indol-3-yl)butyl]piperazin-1-yl}benzofuran -2-yl)methanoyl]piperazine-1-carboxylate. Reaction of the free base with 1N HCl solution in isopropanol gives tert-butyl 4-[1-(5-{4-[4-(5-cyano-1H-indol-3-yl)butyl]piperazin-1-yl}benzofuran-2-yl)methanoyl]piperazine-1-carboxylate, dihydrochloride, m.p. 190–200°. Removal of the protecting group gives
3-(4{4-[2-(1-piperazin-1-ylmethanoyl)benzofuran-5-y]piperazin-1-yl}butyl)-1H-indole-5-carbonitrile. Reaction with HCl solution, as described above, gives 3-(4-{4-[2-(1-piperazin-1-ylmethanoyl)benzofuran-5-yl]piperazin-1-yl}-butyl)-1H-indole-5-carbonitrile, trihydrochloride, m.p. 215°;
1-methylpiperazine gives
3-(4-{4-[2-(4-methylpiperazine-1-carbonyl)benzofuran-5-yl]piperazin-1-yl}-butyl)-1H-indole-carbonitrile. Reaction with HCl solution, as described above, gives 3-(4-{4-[2-(4-methylpiperazine-1-carbonyl)benzofuran-5-yl]piperazin-1-yl}butyl)-1H-indole-5-carbonitrile, dihydrochloride, m.p. 202–204°.

Tert-butoxycarbonylguanidine gives the compound ventional work-up, giving N-hydroxy-5-{4-[4-(5-cyano-1H-indol-3-yl)butyl]piperazin-1-yl}benzofuran-2-carboxamide, m.p. 198–199°.

3. A solution of 1.0 g of 5-{4-[4-(5-cyano-1H-indol-3-yl)butyl]piperazin-1-yl}benzofuran-2-carboxylic acid and 1

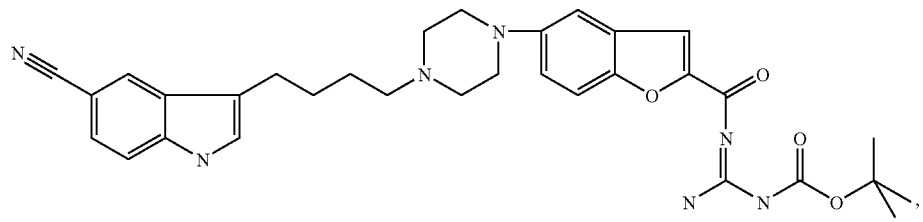

which has a solidification point of 167–168°. Removal of the protecting group gives N-[1-(5-{4-[4-(5-cyano-1H-indol-3-yl)butyl]piperazin-1-yl}benzofuran-2-yl)-methanoyl]guanidine. Reaction with 1N HCl solution in isopropanol gives N-[1-(5-{4-[4-(5-cyano-1H-indol-3-yl)butyl]piperazin-1-yl}benzofuran-2-yl) methanoyl]guanidine, dihydrochloride.

The compound N-[1-(5-{4-[4-(5-cyano-1H-indol-3-yl)butyl]piperazin-1-yl}benzofuran-2-yl)methanoyl]guanidine can also be prepared by removal of the benzyloxycarbonyl group from the compound ml of hydrazinium hydroxide in 10 ml of ethanol is stirred at the boiling point for 18 hours. The reaction mixture is subjected to conventional work-up, giving 5-{4-[4-(5-cyano-1H-indol-3-yl)-butyl]piperazin-1-yl}benzofuran-2-carbohydrazide.

Reaction of the free base with 1N HCl solution in isopropanol gives 5-{4-[4-(5-cyano-1H-indol-3-yl)butyl]piperazin-1-yl}benzofuran-2-carbohydrazide, dihydrochloride, m.p. >215°.

The examples below relate to pharmaceutical preparations:

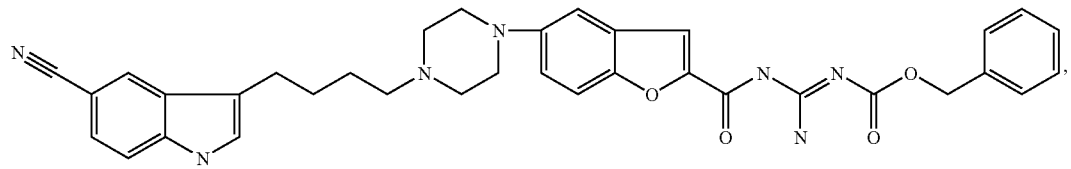

m.p.>231°.

EXAMPLE 4

1. A solution of 2.2 g of 5-{4-[4-(5-cyano-1H-indol-3-yl)butyl]piperazin-1-yl}benzofuran-2-carboxylic acid, 1.4 g of 2-chloro-1-ethylpyridinium iodide, 2.5 ml of N-ethyldiisopropylamine and 0.28 g of cyanamide in 25 ml of 1-methyl-2-pyrrolidone is stirred at room temperature for 18 hours. The reaction mixture is subjected to conventional work-up, giving N-cyano-5-{4-[4-(5-cyano-1H-indol-3-yl)butyl]piperazin-1-yl}benzofuran-2-carboxamide, m.p. 190° C.

Reaction of the free base with 1N HCl solution in isopropanol gives N-carbamoylmethyl-5-{4-[4-(5-cyano-1H-indol-3-yl)butyl]piperazin-1-yl}benzofuran-2-carboxamide hydrochloride.

2. 1.7 g of 2-chloro-1-methylpyridinium chloride are added to a suspension of 2.8 g of 5-{4-[4-(5-cyano-1H-indol-3-yl)butyl]piperazin-1-yl}benzofuran-2-carboxylic acid in 58 ml of 1-methyl-2-pyrrolidone, and the mixture is heated at 50° for 2 hours. 1.15 g of O-(tert-butyidimethylsilyl)hydroxylamine are then added, and 4 ml of Hünig base are added dropwise. The reaction mixture is stirred at room temperature for 18 hours and subjected to con-

Example A: Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised and sealed under sterile conditions. Each injection vial contains 5 mg of active ingredient.

Example B: Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

Example C: Solution

A solution is prepared from 1 g of an active ingredient of the formula I, 9.38 g of $NaH_2PO_4 \times 2H_2O$, 28.48 g of $Na_2HPO_4 \times 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F: Coated Tablets

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is transferred into ampoules, lyophilised under aseptic conditions and sealed under sterile conditions. Each ampoule contains 10 mg of active ingredient.

We claim:

1. A compound of formula I

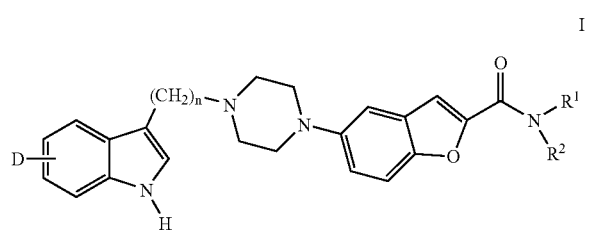

wherein
D is CN,
R$^1$ is Het, unsubstituted or A-substituted cycloalkyl having from 3 to 7 carbon atoms, or unbranched alkyl having from 1 to 6 carbon atoms, with the proviso that at least one CH$_2$ group in the alkyl group has been replaced by an O atom, by a CH=CH group or by a C≡C group, or with the proviso that at least one hydrogen atom in the alkyl group has been replaced by Hal, OH, Ar, Het, cycloalkyl having from 3 to 10 carbon atoms, N(R$^4$)$_2$, CN, CON(R$^4$)$_2$, or NR$^4$COOR$^4$,
R$^2$ is H, A or R$^1$, with the proviso that, if R$^1$ is amino, hydroxyl or cyano, R$^2$ is H, or NR$^1$ R$^2$ together is a three- to 7-membered saturated heterocyclic ring, in which, in addition, 1 or 2 N and/or 1 or 2 S and/or 1 or 2 O atoms and/or one S(O)$_m$ group, which may be substituted by A, Hal, cycloalkyl having from 3 to 10 carbon atoms, OR$^4$, N(R$^4$)$_2$, CN, COOR$^4$, CON(R$^4$)$_2$, NR$^4$COR$^4$ and/or carbonyl oxygen, may be present, R$^3$ is OH, OA or N(R$^4$)$_2$, R$^4$ is H or A, A is unbranched or branched alkyl having from 1 to 6 carbon atoms, in which at least one CH$_2$ group may be replaced by an O or S atom or by a CH=CH group, or at least one H atom may be replaced by F, Ar is phenyl, naphthyl or biphenyl, each of which is unsubstituted or monosubstituted or polysubstituted by Hal, A, OR$^4$, N(R$^4$)$_2$, NO$_2$, CN, COOR$^4$, CON(R$^4$)$_2$, NR$^4$COR$^4$, NR$^4$CON(R$^4$)$_2$, NR$^4$SO$_2$A, COR$^4$, SO$_2$NR$^4$ or S(O)$_m$A, Het is a saturated, unsaturated or aromatic monocyclic or bicyclic heterocyclic radical having from 5 to 10 ring members, in which from 1 to 4 N and/or from 1 to 4 S and/or from 1 to 4 O atoms may be present, and the heterocyclic radical may be monosubstituted, disubstituted or trisubstituted by Hal, A, —[C(R$^4$)$_2$]$_o$—Ar, —[C(R$^4$)$_2$]$_o$-cycloalkyl, OR$^4$, N(R$^4$)$_2$, NO$_2$, CN, COOR$^4$, CON(R$^4$)$_2$, NR$^4$COA, NR$^4$CON(R$^4$)$_2$, NR$^4$SO$_2$A, COR$^4$, SO$_2$NR$^4$ S(O)$_m$A and/or carbonyl oxygen, Hal is F, Cl, Br or I, n is 4, m is 1 or 2, o is 0, 1, 2, 3 or 4, or a physiologically acceptable salt thereof or solvate thereof.

2. A compound according to claim 1 selected from the group consisting of:
  a) N-(2-methoxyethyl)-5-{4-[4-(5-cyano-1H-indol-3-yl)butyl]piperazin-1-yl}benzofuran-2-carboxamide,
  b) N-carbamoylmethyl-5-{4-[4-(5-cyano-1H-indol-3-yl)butyl]piperazin-1-yl}benzofuran-2-carboxamide,
  c) N-(2-hydroxyethyl)-5-{4-[4-(5-cyano-1H-indol-3-yl)butyl]piperazin-1-yl}benzofuran-2-carboxamide,
  d) N-(pyridin-2-ylmethyl)-5-{4-[4-(5-cyano-1H-indol-3-yl)butyl]piperazin-1-yl}benzofuran-2-carboxamide,
  e) N-(pyridin-4-ylmethyl)-5-{4-[4-(5-cyano-1H-indol-3-yl)butyl]piperazin-1-yl}benzofuran-2-carboxamide,
  f) N-(2-methylaminoethyl)-5-{4-[4-(5-cyano-1H-indol-3-yl)butyl]piperazin-1-yl}benzofuran-2-carboxamide,
  g) N-(2-aminoethyl)-5-{4-[4-(5-cyano-1H-indol-3-yl)butyl]piperazin-1-yl}-benzofuran-2-carboxamide,
  h) N-(2-aminoethylmethyl)-5-{4-[4-(5-cyano-1H-indol-3-yl)butyl]piperazin-1-yl}benzofuran-2-carboxamide,
  i) N-(2-methylaminoethylmethyl)-5-{4-[4-(5-cyano-1H-indol-3-yl)butyl]piperazin-1-yl}benzofuran-2-carboxamide,
  j) N-(piperidin-4-ylmethyl)$_5$-{4-[4-(5-cyano-1H-indol-3-yl)butyl]piperazin-1-yl}benzofuran-2-carboxamide or
  k) N-piperidin-4-yl-5-{4-[4-(5-cyano-1H-indol-3-yl)butyl]piperazin-1-yl}benzofuran-2-carboxamide, a physiologically acceptable salt thereof and a physiologically acceptable solvate thereof.

3. Process for the preparation of compounds of formula I according to claim 1, comprising reacting
a) a compound of the formula II

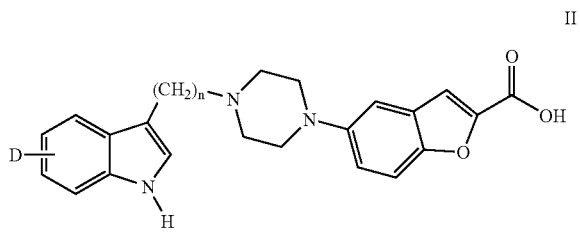

wherein D and n are as defined in claim 1, with a compound of the formula III or a salt thereof

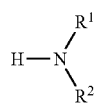

wherein $R^1$ and $R^2$ are as defined in claim 1, or
b) a compound of the formula IV

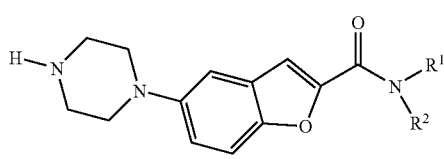

wherein $R^1$ and $R^2$ are as defined in claim 1, with a compound of the formula V wherein L is Cl, Br, I or a free or reactively functionally modified OH group, and D and n are as defined in claim 1, and optionally
c) converting one of the radicals D, $R^1$ and/or $R^2$ into another radical D, $R^1$ and/or $R^2$ by, for example, cleaving an OA group to form an OH group and/or converting a CHO group into a CN group, and/or
further converting a resultant base of the formula I into one of its salts by treatment with an acid.

4. A pharmaceutical composition comprising at least one compound of claim 1 and a pharmaceutically acceptable carrier.

5. A compound according to claim 1, wherein the solvate is a hydrate or an alcoholate.

6. A pharmaceutical composition of claim 4 wherein the additional ingredient is a solid, liquid, or a semi-solid excipient and/or an assistant.

7. A pharmaceutical composition of claim 5 wherein the excipient is water, vegetable oils, benzyl alcohols, alkylene glycols, polyethylene glycols, glycerol triacetate, gelatine, carbohydrates, magnesium stearate, talc, or Vaseline and the assistant is a lubricant, preservative, stabilizer, wetting agent, emulsifier, a salt for modifying the osmotic pressure, a buffer substance, a dye, or a flavor.

8. A pharmaceutical composition of claim 4 wherein the additional ingredient is a vitamin or citalopram hydrobromide.

9. A pharmaceutical composition of claim 4 comprising a compound of formula I in doses of between 0.1 and 500 mg per dosage unit, said compound being administered from between 0.001 and 10mg/kg of body weight.

10. A pharmaceutical composition of claim 4 wherein a compound of formula I is prepared in the form of solutions, suspensions, emulsions, lyophilisates, tablets, pills, coated tablets, capsules, powders, granules, syrups, juices, drops, suppositories, implants, ointments, creams, or powders.

11. A compound of claim 1 wherein A is methyl, ethyl, n-propyl, isopropyl, n-butyl, sec-butyl, tert-butyl, pentyl, 1-, 2-or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethyl-butyl, 1-ethyl-1-methylpropyl, 1-ethyl-2-methylpropyl, 1,1,2- or 1,2,2-trimethylpropyl, trifluoromethyl, pentafluoroethyl, heptafluoropropyl, methoxymethyl, methoxyethyl, methoxypropyl, ethoxymethyl, ethoxyethyl, ethoxypropyl, methylsulfanylmethyl, methylsulfanylethyl, methylsulfanylpropyl, ethylsulfanylmethyl, ethylsulfanylethyl, ethylsulfanylpropyl, allyl, propenyl, but-2-enyl, but-3-enyl, pent-3-enyl, pent-4-enyl or hex-3-enyl.

12. A compound of claim I wherein A is methyl or tert-butyl.

13. A compound of claim 1 wherein Ar is phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-trifluoromethylphenyl, o-, m- or p-hydroxyphenyl, o-, m- or p-nitrophenyl, o-, m- or p-(trifluoromethoxy) phenyl, o-, m- or p-cyano-phenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-(difluoromethoxy)phenyl, o-, m- or p-(fluoromethoxy) phenyl.

14. A compound of claim 1 wherein Ar is phenyl.

15. A compound of claim 1 wherein Hal is fluorine, chlorine, or bromine.

16. A compound of claim 1 wherein Hal is fluorine.

17. A compound of claim 1 wherein Het is furan-2-yl, tetrahydrofuran-2-yl, pyridin-4-yl, pyridin-3-yl, pyridin-2-yl, thiophen-2-yl or imidazol-5-yl.

18. A compound of claim 1 wherein $R^1$ is 2-aminoethyl, 2-methylaminoethyl, piperidin-4-ylmethyl or piperidin-4-yl.

19. A compound of claim 1 wherein $R^2$ is H or methyl.

* * * * *

UNITED STATES PATENT AND TRADEMARK OFFICE
CERTIFICATE OF CORRECTION

PATENT NO.        : 7,244,846 B2  
APPLICATION NO. : 10/471584  
DATED             : July 17, 2007  
INVENTOR(S)       : Dieter Dorsch Page 1 of 1

It is certified that error appears in the above-identified patent and that said Letters Patent is hereby corrected as shown below:

Column 22, line 19 reads "$SO^2NR^4$", should read -- $SO_2NR^4$ --  
Column 22, line 61 reads "ylmethyl)$_5$" should read -- ylmethyl)5 --  
Column 23, line 1 reads "preparation of compounds" should read -- preparation of a compound --

Signed and Sealed this

Fifteenth Day of April, 2008

JON W. DUDAS  
*Director of the United States Patent and Trademark Office*